(12) United States Patent
Lambert et al.

(10) Patent No.: US 6,284,265 B1
(45) Date of Patent: Sep. 4, 2001

(54) ANTACID FORMULATION

(75) Inventors: David H. Lambert, Midway, KY (US); Richard S. Kaster, Oneida, WI (US); J. Mark Glyer, Lexington; Joe D. Pagan, Versailles, both of KY (US)

(73) Assignee: KPL Technologies, Inc., Midway, KY (US)

( * ) Notice: Subject to any disclaimer, the term of this patent is extended or adjusted under 35 U.S.C. 154(b) by 0 days.

(21) Appl. No.: 09/041,565

(22) Filed: Mar. 12, 1998

Related U.S. Application Data

(60) Provisional application No. 60/040,359, filed on Mar. 13, 1997.

(51) Int. Cl.$^7$ .............................. A61K 47/00; A61K 9/20; A61K 9/14
(52) U.S. Cl. ......................... 424/439; 424/464; 424/465; 424/484
(58) Field of Search ..................................... 424/439, 464, 424/484, 465; 514/819

(56) References Cited

U.S. PATENT DOCUMENTS 4,327,076 * 4/1982 Puglia .

OTHER PUBLICATIONS

The Merck Index; Eleventh Edition; 1989; Entries 362, 3169, 1699 and 1657.

The Merck Index, 12th edition, 1996, pp. 3794–3795.*

* cited by examiner

*Primary Examiner*—Thurman K. Page
*Assistant Examiner*—Amy E Pulliam
(74) *Attorney, Agent, or Firm*—King and Schickli PLLC

(57) ABSTRACT

An antacid formulation comprises 11.0–45.0% antacid selected from a group consisting of aluminum phosphate, dihydroxy-aluminum-sodium-carbonate, dicalcium phosphate, calcium carbonate and mixtures thereof, 4.0–8.0 oil, 0.02–1.0% antioxidant and 46.0–84.5% carrier.

3 Claims, No Drawings

ANTACID FORMULATION

This patent application claims the benefit of U.S. Provisional Patent Application Serial No. 60/040,359, filed Mar. 13, 1997, entitled "Acid Formulation".

TECHNICAL FIELD

The present invention relates generally to the animal husbandry field and, more particularly, to an antacid formulation adapted for administration to horses.

BACKGROUND OF THE INVENTION

Many horses suffer from excess gastric acid secretions when receiving high grain, low forage diets. This is particularly true of horses under "heavy work" conditions including race training, eventing and polo competitions. It is also true of young horses which are receiving such diets in order to promote growth. A high grain-low forage diet is defined as more than 5 kgs (11 lbs) of concentrate feed per day or a forage to grain ratio of less than 1:1.

As a more detailed example, studies have shown that between 80–90% of racehorses in training have gastric ulcers occur in the fundus, the nonglandular region of the stomach located above the margo plicatus. The fundus consists of squamous epithelial cells that are similar to the tissue found in the esophagus. The cells in the fundus do not have a mucus layer. Further, the fundus cells do not secrete bicarbonate. Accordingly, the only protection these cells have from gastric acid is furnished by saliva which provides a natural buffering effect.

Race horses in training are often fed high grainlow forage diets. Unfortunately, grains and pelleted concentrates have a tendency to increase the production of gastrin: a hormone that stimulates gastric acid production. Often race horses in training are fasted for extended periods of time before a training exercise, workout or race. This fasting has a tendency to reduce saliva production. Thus, race horse management and handling has the unfortunate effect of promoting higher levels of gastric production and lower levels of saliva production. This results in the exposure of the fundus to gastric acid at lower pH levels for longer periods of time without effective buffering from saliva production. As a consequence gastric irritation occurs and often lesions develop. Thus, it should be appreciated that gastric acid is the major cause of ulcers in the fundus region of the stomach.

The present invention relates to an antacid formulation specifically adapted to aid in the reduction of excess gastric acid secretion in horses suffering from this malady.

SUMMARY OF THE INVENTION

It is, accordingly, one object of the present invention to provide antacid formulations for the safe and effective treatment and relief of excess gastric acid secretions.

A further object of the present invention is to provide an antacid formulation particularly effective in reducing excess gastric acid secretions in horses resulting from a high grain-low forage diet.

Still another object of the present invention is to provide a safe and effective method of reducing excess gastric acid secretions and to coat and protect the mucosa from gastric acid irritation in horses.

Other objects and advantages of the present invention will become apparent as the description thereof proceeds.

In satisfaction of the foregoing objects and advantages, there is provided by this invention, an antacid formulation comprising by weight percent:

11.0–45.0% antacid selected from a group consisting of aluminum phosphate, dihydroxy-aluminum-sodium-carbonate, dicalcium phosphate, calcium carbonate and mixtures thereof;
4.0–8.0% oil;
0.02–1.0% antioxidant; and
46.0–84.5% carrier.

More specifically, the antacid formulation includes ethoxyquin as the antioxidant and utilizes a vegetable oil such as soybean oil. Preferably, the carrier utilized is selected from a group consisting of ground wheat, spray dried whey, steam rolled oats and mixtures thereof.

More specifically describing the invention, the antacid formulation includes by weight percent between:

5.0–15.0% aluminum phosphate;
5.0–15.0% dihydroxy-aluminum-sodium-carbonate;
4.0–8.0% soybean oil;
1.0–5.0% dicalcium phosphate;
0–10.0% calcium carbonate;
0.02–1.0% ethoxyquin; and
46.0–84.5% carrier.

Still more specifically, the antacid formulation comprises by weight percent:

10.0% dihydroxy-aluminum-sodium-carbonate;
10.0% aluminum phosphate;
6.0% soybean oil;
2.75% dicalcium phosphate;
0.7% calcium carbonate;
0.1% ethoxyquin; and
70.45% carrier (30.45% ground wheat, 20.0% spray dried whey and 20.0% steam rolled oats).

DETAILED DESCRIPTION OF THE INVENTION

As indicated above, the present invention is drawn to a novel antacid formulation containing an effective amount of antacid so as to be useful in reducing excess gastric acid secretion in horses. This includes but is not particularly limited to the reduction of excess gastric acid secretions in horses and foals resulting from high grain-low forage diets often fed to such animals in order to provide the desired energy level for heavy work or nutrition to provide rapid growth.

The antacid formulation comprises by weight percent 11.0–45.0% antacid. Preferably, the antacid is selected from a group consisting of aluminum phosphate, dihydroxy-aluminum-sodium-carbonate, dicalcium phosphate, calcium carbonate and mixtures thereof. These compounds all reduce gastric acid levels in the animal to which the antacid formulation is administered.

Specifically, dihyrdoxy-aluminum-sodium-carbonate provides strong buffering action to reduce gastric acid pH. Aluminum phosphate provides some buffering and coats and protects the mucosa from gastric acid irritation. Dicalcium phosphate and calcium carbonate provide some buffering and may also be effectively utilized to balance the calcium to phosphorous ratio for best nutrition.

Magnesium hydroxide is not utilized since horses are sensitive to this compound which has a tendency at high dosage rates to produce an ataxic effect.

As a precaution against the possibility that an aluminum based antacid will interfere with phosphorous adsorption, preferably the formulation incorporates a phosphrous supplement in some form. The phosphorous is balanced with supplemental calcium in a ratio of calcium to phosphorous between 1:1–3:1 so as to insure a formulation consistent with the nutritional needs of the horse.

Additionally, the antacid formulation includes 4.0–8.0% oil. Preferably, the oil is in the form of vegetable oil such as soybean or corn oil. This oil increases the palletablity of the formulation and also aids in the pelleting process.

Still further, the antacid formulation includes 0.02–1.0% antioxidant. Preferably, the antioxidant utilized in ethoxyquin. The antioxidant functions to prevent oxidation and breakdown of certain components of the composition prior to consumption by the animal.

Finally, the antacid formulation includes 46.0–84.5% carrier. Preferably, the carrier utilized is selected from a group consisting of ground wheat, spray dried whey, steam rolled oats and mixtures thereof. Of course, other carriers known in the art may be utilized if desired.

More particularly describing the invention, the antacid formulation consists by weight percent essentially of:

5.0–15.0% aluminum phosphate;
5.0–15.0% dihydroxy-aluminum-sodium-carbonate;
4.0–8.0% soybean oil;
1.0–5.0% dicalcium phosphate;
0.0–10.0% calcium carbonate;
0.02–1.0% ethoxyquin; and
46.0–84.5% carrier.

Still more specifically, the antacid formulation comprises by weight percent substantially:

10.0% dihydroxy-aluminum-sodium-carbonate;
10.0% aluminum phosphate;
6.0% soybean oil;
2.75% dicalcium phosphate;
0.7% calcium carbonate;
0.1% ethoxyquin; and
70.45% carrier.

The 70.45% carrier is broken down as 30.45% ground wheat, 20.0% spray dried whey and 20.0% steam rolled oats.

The antacid formulation is preferably made by simply mixing the ingredients in, for example, a batch mixer. Following mixing, the formulation may be pelletized in accordance with procedures well known to those skilled in the art.

The method of treating the horses, includes the step of feeding an animal between 60–120 grams (2–4 ozs.) of the formulation with each grain meal of approximately 2–5 lbs of grain. For adult horses, the total daily intake of the antacid composition is not to exceed 454 grams (16 ozs.). For foals and young growing horses, the total daily intake of the antacid formulation is not to exceed 240 grams or approximately 8 ozs.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. An antacid formulation, comprising by weight percent:

11.0–45.0% antacid selected from a group consisting of aluminum phosphate, dihydroxy-aluminum-sodium-carbonate, dicalcium phosphate, calcium carbonate and mixtures thereof;
4.0–8.0% oil;
0.02–1.0% antioxidant; and
46.0–84.5% carrier wherein said carrier is selected from a group consisting of ground wheat, spray dried whey, steam rolled oats and mixtures thereof.

2. An antacid formulation, consisting essentially of by weight percent:

5.0–15.0% aluminum phosphate;
5.0–15.0% dihydroxy-aluminum-sodium-carbonate;
4.0–8.0% soybean oil;
1.0–5.0% dicalcium phosphate;
0.0–10.0% calcium carbonate;
0.02–1.0% ethox quin; and
46.0–84.5% carrier wherein said carrier is selected from a group consisting of ground wheat, spray dried whey, steam rolled oats and mixtures thereof.

3. An antacid formulation, comprising by weight percent substantially:

10.0% dihydroxy-aluminum-sodium-carbonate;
6.0% soybean oil;
2.75% dicalcium phosphate;
0.7% calcium carbonate;
0.1% ethoxyquin; and
70.45% carrier wherein said carrier is 30.45% ground wheat, 20.0% spray dried whey, and 20.0% steam rolled oats.

* * * * *